United States Patent [19]
Bennett

[11] 4,055,643
[45] Oct. 25, 1977

[54] FURO(3,4-e)-AS-TRIAZINES AND CORRESPONDING 4-OXIDES AS SLEEP INDUCERS AND MINOR TRANQUILIZERS

[75] Inventor: Gregory B. Bennett, Mendham, N.J.

[73] Assignee: Sandoz, Inc., E. Hanover, N.J.

[21] Appl. No.: 665,775

[22] Filed: Mar. 10, 1976

Related U.S. Application Data

[60] Division of Ser. No. 586,349, June 12, 1975, Pat. No. 3,963,713, which is a continuation-in-part of Ser. No. 541,721, Jan. 17, 1975, abandoned, which is a continuation-in-part of Ser. No. 496,578, Aug. 12, 1974, abandoned, which is a continuation-in-part of Ser. No. 465,759, May 1, 1974, abandoned.

[51] Int. Cl.² .............................................. A61K 31/53
[52] U.S. Cl. ....................................................... 424/249
[58] Field of Search ................. 424/249; 260/248 AS, 260/586, 349

[56] References Cited
U.S. PATENT DOCUMENTS 3,697,518  10/1972  Schmidt et al. ................... 260/248
3,772,276  11/1973  Sauter .................................. 260/248

Primary Examiner—Albert T. Meyers
Assistant Examiner—Daren M. Stephens
Attorney, Agent, or Firm—Gerald D. Sharkin; Robert S. Honor; Timothy G. Rothwell

[57] ABSTRACT 5,5,7,7-tetramethyl-3-substituted or unsubstituted-phenylfuro[3,4-e]-as-triazines and corresponding 4-oxides, e.g., 5,7-dihydro-5,5,7,7-tetramethyl-3-phenyl-furo[3,4-e]-as-triazine and 5,7-dihydro-5,5,7,7-tetramethyl-3-phenylfuro[3,4-e]-as-triazine-4-oxide, are prepared from 2,2,5,5-tetramethyl-3,4(2H,5H)-furandione-3-hydrazone-4-oximes and are useful as sleep inducers and minor tranquilizers.

3 Claims, No Drawings

FURO(3,4-e)-AS-TRIAZINES AND CORRESPONDING 4-OXIDES AS SLEEP INDUCERS AND MINOR TRANQUILIZERS

This application is a division of copending application Ser. No. 586,349, filed June 12, 1975 which issued as U.S. Pat. No. 3,963,713 on June 15, 1976, which in turn is a continuation-in-part of copending application Ser. No. 541,721, filed Jan. 17, 1975, now abandoned, which in turn is a continuation-in-part of copending application Ser. No. 496,578, filed Aug. 12, 1974, now abandoned, which in turn is a continuation-in-part of copending application Ser. No. 465,759, filed May 1, 1974, now abandoned.

This invention relates to furo[3,4-e]-as-triazines and corresponding 4-oxides which exhibit sleep inducer and minor tranquilizer activity. In particular, it relates to 5,5,7,7-tetramethyl-3-substituted or unsubstituted-phenylfuro[3,4-e]-as-triazines and corresponding 4-oxides, pharmaceutically acceptable salts, their preparation and intermediates thereof.

The compounds of this invention may be represented by the following structural formula:

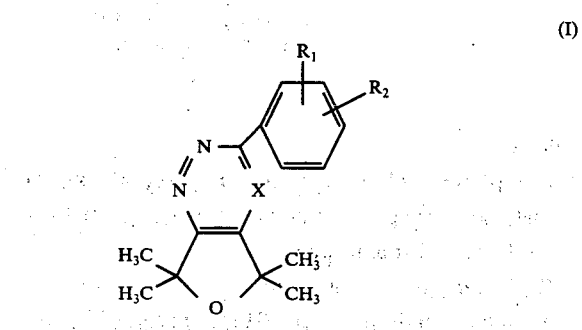

wherein
$R_1$ and $R_2$ each independently represent hydrogen having an atomic weight of about 19 to 36, lower alkyl, i.e., alkyl having 1 to 4 carbon atoms, e.g., methyl, ethyl, isopropyl and the like, straight chain lower alkoxy, i.e., alkoxy having 1 to 4 carbon atoms, e.g., methoxy, ethoxy and the like, amino, nitro or trifluoromethyl, and
X represents

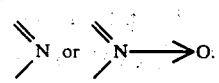

provided that
i. when one of $R_1$ and $R_2$ represents nitro, the other is other than nitro or trifluoromethyl;
ii. when $R_1$ and $R_2$ represent trifluoromethyl, they are on other than adjacent carbon atoms, and
iii. when $R_1$ and $R_2$ represent t-butyl, they are on other than adjacent carbon atoms.
iv. when one of $R_1$ and $R_2$ is trifluoromethyl and the other is t-butyl, they are on other than adjacent carbon atoms, The compounds of formula (I) in which X represents

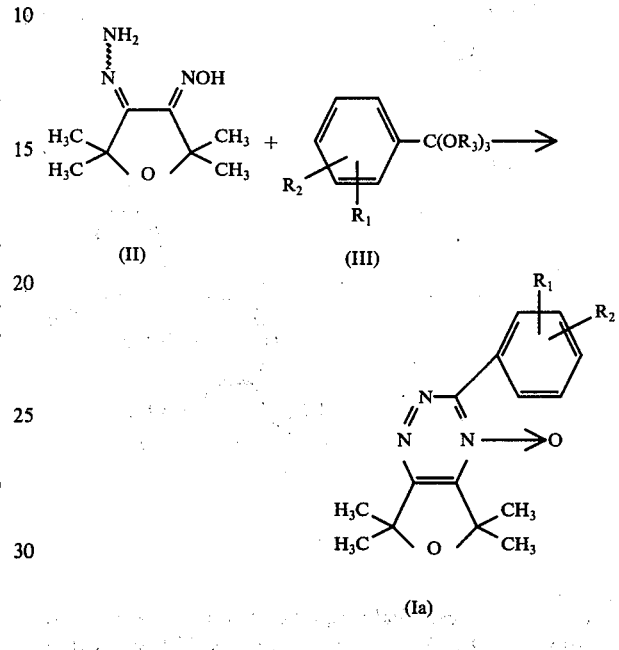

may be prepared according to the following reaction scheme:

where
$R_3$ represents lower alkyl having 1 to 2 carbon atoms, i.e., methyl or ethyl, and
$R_1$, $R_2$ and the provisos are as defined above.

The compounds of formula (Ia) are prepared by treating a compound of the formula (II) with a compound of the formula (III) in the presence of an inert atmosphere, e.g., nitrogen, helium or argon and in the presence of an inert organic solvent. Although the particular solvent employed is not critical, the preferred solvents include the aromatic hydrocarbons such as benzene, toluene and the like, the lower alkanols such as methanol, ethanol and the like, or an excess of the ortho ester of formula (III), the latter being especially preferred. The temperature of the reaction is not critical, but it is preferred that the reaction be run from about 70° to 200° C., preferably from about 130° to 150° C. The reaction is run from about 12 to 36 hours, preferably from about 15 to 20 hours. The product is recovered using conventional techniques, e.g., filtration.

Another aspect of this invention and the preferred method of preparing the compounds of formula (I) in which X represents and one of $R_1$ and $R_2$ is nitro and the other is other than nitro or trifluoromethyl may be illustrated by the following reaction scheme:

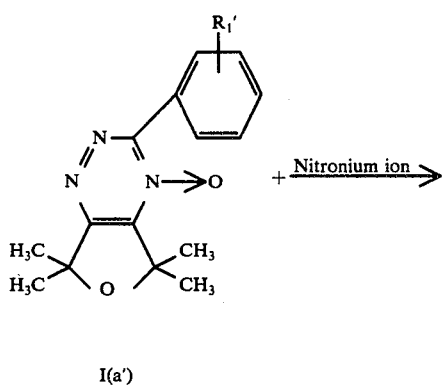

I(a')

+ Nitronium ion →

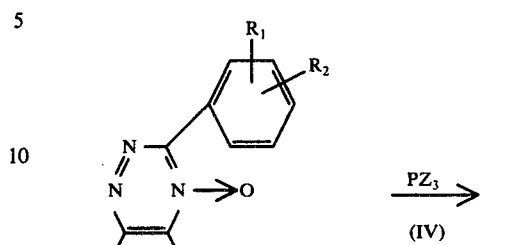

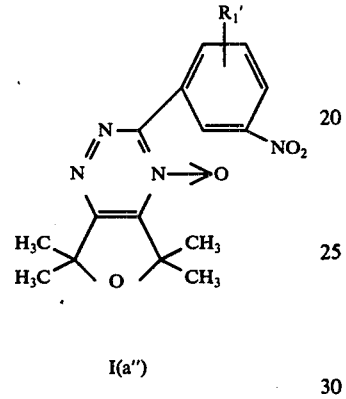

I(a'')

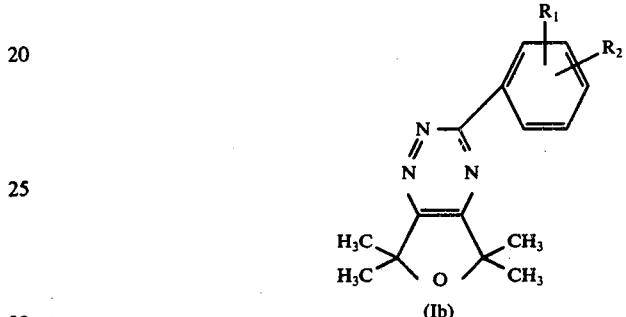

where
R₁' is hydrogen, halo having an atomic weight of about 19 to 36, lower alkyl, i.e., alkyl having 1 to 4 carbon atoms, e.g., methyl, ethyl and the like, straight chain lower alkoxy, i.e., alkoxy having 1 to 4 carbon atoms, e.g., methoxy, ethoxy and the like, or amino.

The compounds of formula I(a'') may be prepared by treating a compound of formula I(a') with a nitronium iron-forming reactant in the presence of an inert organic solvent. The nitronium iron-forming reactant may be prepared, for example, from a mixture of sulfuric acid and nitric acid, a mixture of trifluoromethanesulfonic acid with fuming nitric acid, or a mixture of hydrogen fluoride, and dinitrogen peroxide in nitromethane at −20° C. saturated with boron fluoride, preferably trifluoromethane sulfonic acid with fuming nitric acid, in a ratio of 2 moles trifluoromethanesulfonic acid to 1 mole of fuming nitric acid. Although the particular solvent used is not critical, the preferred solvents include the aromatic hydrocarbons such as benzene, toluene and the like or the halogenated hydrocarbons such as methylene chloride chloroform and the like, preferably methylene chloride. The temperature of the reaction is not critical, but it is preferred that the reaction be run from about −80° C. to +70° C., preferably from about −35° C. to +30° C. The reaction is run from about 19 to 96 hours, preferably from about 60 to 75 hours. The product is recovered using conventional techniques, e.g., recrystallization.

The compounds of formula (I) in which X represents

may be prepared according to the following reaction scheme:

where
Z represents chloro, bromo or lower alkoxy, i.e., alkoxy having 1 to 4 carbon atoms, e.g., methoxy, ethoxy and the like, and
R₁, R₂, and the provisos are as defined above.

The compounds of formula (Ib) are prepared by treating a compound of the formula (Ia) with a compound of the formula (IV) in the presence of an inert atmosphere, e.g., nitrogen, helium or argon, and in the presence of an inert organic solvent. Although the particular solvent used is not critical, the preferred solvents include the aromatic hydrocarbons such as benzene, toluene and the like, or an excess of the trivalent phosphorus compound of the formula (IV), the latter being especially preferred. The temperature of the reaction is not critical, but it is preferred that the reaction be run from 100° to 210° C., preferably from about 140° C. to 170° C. The reaction is run from about 12 to 36 hours, preferably from about 15 to 20 hours. The product is recovered using conventional techniques, e.g., crystallization.

The compounds of formula (I) in which X represents may also be prepared according to the following reaction scheme which is preferred:

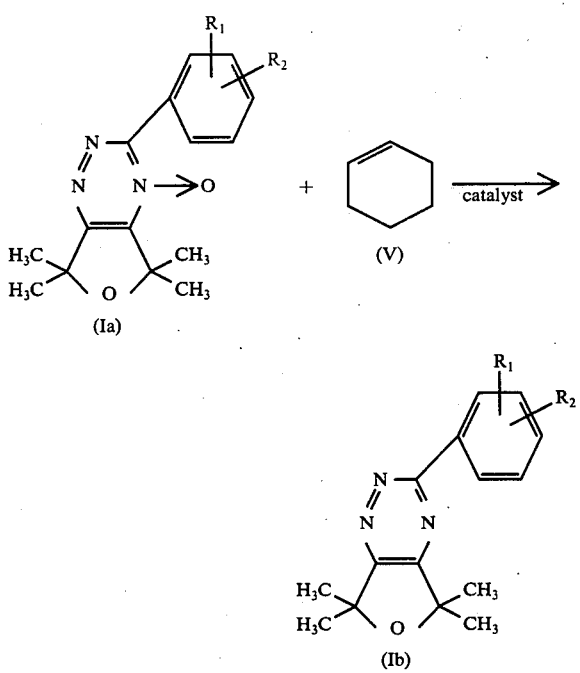

where $R_1$, $R_2$, and the provisos are as defined above.

The compounds of formula (Ib) are prepared by treating a compound of the formula (Ia) with cyclohexene in an inert atmosphere, e.g., nitrogen, helium, or argon, preferably nitrogen, and in the presence of a noble metal catalyst such as palladium, platinum, rhodium and the like, preferably palladium, optionally neat or on a support such as charcoal, in an inert organic solvent. Although the particular solvent used is not critical, it is preferred that the reaction be carried out in the presence of the lower alkanols, e.g., methanol, ethanol, and the like, preferably ethanol. Temperature of the reaction is not critical but it is preferred that the reaction be carried out between about 20° to 200° C., preferably from about 70° to 110° C. The reaction is run from about 5 to 72 hours, preferably from about 15 to about 30 hours. The product is recovered using conventional techniques, e.g., crystallization.

Certain of the compounds of formulae (II), (III), and (IV) are known and may be prepared by methods described in the literature. Those compounds of formulae (II), (III), and (IV) not specifically disclosed may be prepared by analogous methods from known starting materials.

The compounds of formula (I) are useful because they possess pharmacological activity in animals as sleep inducers and minor tranquilizers as indicated (1) by the hexobarbital reinduction method of Winter, J. Pharmacol. and Exp. Therap., 94, 7-11, 1948; (2) as indicated in the Cebus monkey using chronically implanted electrodes. Brain readings are obtained via a 10 or 16 channel electroencephalograph. For the recording sessions, the monkeys are restrained by neck and waist plates in chairs in full side observation cages at the same time every night for 13½ hours Monday through Thursday. Gross behavior is monitored via closed circuit television and video tape recordings. The compound of formula (I) is administered p.o. immediately on placing the monkey in the observation cages with at least 7 days intervening between drug administration. Physiological saline is administered via a similar route and at the same time on all control runs. Control data are collected at least 3 days per week and accumulated to give control data for 15 sessions per monkey Data from each session are statistically compared via computer analysis to the previous 5-15 control sessions for the particular animal, with particular emphasis given to the following phases of the sleep-wakefulness cycle: resting awake, light sleep, deep sleep, paradoxical (REM) sleep, "pseudo-"paradoxical sleep, latency to onset of deep sleep, and latency to onset of first epoch of paradoxical sleep; (3) by their ability to produce docility in behavior tests in mice given 25 to 200 mg/kg of animal body weight, i.p. of the test compound according to the 30-word adjective check sheet system basically as described by Irwin S. (Gordon Research Conference, Medicinal Chemistry, 1959) and Chen (Symposium on Sedative and Hypnotic Drugs, Williams and Wilkins, 1954); (4) by their ability to antagonize chronic convulsions and death in mice given 45 to 250 mg/kg i.p. of N-sulfamoylazepine; (5) by scoring for loss of righting reflex according to the method of Reed-Muench (American Journal of Hygiene, 27: 493-497, 1938), in which mice are administered 12.5 mg/kg, i.p. Thioridazine, immediately after which test compound is administered at dosages of 5 to 100 mg/kg in a volume of 0.1 ml/10 g. body weight. Sixty minutes after dosing, the mice are scored for loss of right reflex, and (6) by their ability to reduce conflicts as defined in the Geller Conflict Test (Irving Geller, Psychopharmacologia, Volume I, Page 42-492, 1960).

The sleep inducing effective dosage of the compounds of formula (I) will vary depending on the particular compound employed. However, in general, satisfactory results are obtained when the compounds are administered orally at a daily dosage of from about 0.2 milligrams to about 100 milligrams per kilogram of animal body weight, typically given in a single dose at bedtime. For most large mammals, the total daily dosage is from about 20 to about 750 milligrams, preferably at bedtime and dosage forms suitable for internal administration comprise from about 5 to about 375 milligrams of the compound in admixture with a solid or liquid pharmaceutical carrier or diluent. The preferred pharmaceutical compositions from the standpoint of preparation and ease of administration are solid compositions, particularly hard-filled capsules and tablets.

For minor tranquilizer use, the effective dosage will vary depending on the particular compound employed. However, in general, satisfactory results are obtained when the compounds are administered orally at a daily dosage of from about 0.2 milligrams to about 200 milligrams per kilogram of animal body weight, typically given in divided doses two to four times per day. For most large mammals, the total daily dosage is from about 20 to about 1000 milligrams, and dosage forms suitable for internal administration comprise from about 5 to about 500 milligrams of the compound in admixture with a solid or liquid pharmaceutical carrier or diluent.

The compounds of formula (I) may be similarly administered in the form of their non-toxic pharmaceutically acceptable salts. Such salts possess the same order of activity as the free base and are readily prepared by reacting the base with an appropriate acid by conventional technique and, accordingly, are included within the scope of this invention. Representative of such salts are the mineral acid salts, e.g., hydrochloride, hydrobromide, sulfate and the like, and the organic acid salts such as succinate, benzoate, maleate and the like.

Tablets and capsules containing the ingredients indicated below may be prepared by conventional techniques and are useful as sleep inducers at a dose one or two tablets just before bedtime. Tablets and capsules containing the ingredients indicated below may also be useful as minor tranquilizers in divided doses two to four times per day.

| Ingredients | Weight (mg.) tablet | capsule |
|---|---|---|
| 5,7-dihydro-5,5,7,7-tetramethyl-3-phenylfuro[3,4-e]-as-triazine-4-oxide hydrochloride | 200 | 200 |
| tragacanth | 10 | — |
| lactose | 247.5 | 300 |
| corn starch | 25 | — |
| talcum | 15 | — |
| magnesium stearate | 2.5 | — |
| Total | 500 mg. | 500 mg. |

EXAMPLE 1

5,7-Dihydro-5,5,7,7-tetramethyl-3-phenylfuro[3,4-e]-as-triazine-4-oxide hydrochloride A mixture of 6.84 grams (0.04mole) 2,2,5,5-tetramethyl-3,4(2H,5H)-furandione-3-hydrazone-4-oxime and 15 ml. triethylorthobenzoate is refluxed under nitrogen for 18 hours at a bath temperature of 140° C. The resulting solution is heated for an additional 8 hours maintaining the temperature at 140° C. during which time all distillate is removed. The resulting mixture is cooled to 25° C. and 100 ml. of ether is added. The resulting solid is removed by filtration and the filtrate evaporated to dryness in vacuo at 100° C. The resulting residue is dissolved in ether and the solution saturated with hydrogen chloride gas and filtered to give 5,7-dihydro-5,5,7,7-tetramethyl-3-phenylfuro[3,4-e]-as-triazine-4-oxide hydrochloride, m.p. 154°–156° C.

Following the above procedure and using in place of triethylorthobenzoate an equivalent amount of a. p-chloro-triethylorthobenzoate,
b. p-methyl-triethylorthobenzoate,
c. p-methoxy-triethylorthobenzoate,
d. m-trifluoromethyl-triethylorthobenzoate,
e. p-amino-triethylorthobenzoate,
f. p-nitro-triethylorthobenzoate,
g. 3,4-dichloro-triethylorthobenzoate,
h. m-nitro-triethylorthobenzoate,
i. m-chloro-triethylorthobenzoate,
j. p-fluoro-triethylorthobenzoate,
k. 3,5-dinitro-triethylorthobenzoate, or
l. 3,4-dimethyl-triethylorthobenzoate, there is obtained a. 5,7-dihydro-5,5,7,7-tetramethyl-3-(p-chlorophenyl)-furo[3,4-e]-as-triazine-4-oxide,
b. 5,7-dihydro-5,5,7,7-tetramethyl-3-(p-tolyl)-furo[3,4-e]-as-triazine-4-oxide,
c. 5,7-dihydro-5,5,7,7-tetramethyl-3-(p-anisyl)-furo[3,4-e]-as-triazine-4-oxide,
d. 5,7-dihydro-5,5,7,7-tetramethyl-3-(m-trifluoromethylphenyl)-furo[3,4-e]-as-triazine-4-oxide,
e. 5,7-dihydro-5,5,7,7-tetramethyl-3-(p-aminophenyl)-furo[3,4-e]-as-triazine-4-oxide,
f. 5,7-dihydro-5,5,7,7-tetramethyl-3-(p-nitrophenyl)-furo[3,4-e]-as-triazine-4-oxide,
g. 5,7-dihydro-5,5,7,7-tetramethyl-3-(3,4-dichlorophenyl)-furo[3,4-e]-as-triazine-4-oxide,
h. 5,7-dihydro-5,5,7,7-tetramethyl-3-(m-nitrophenyl)-furo[3,4-e]-as-triazine-4-oxide,
i. 5,7-dihydro-5,5,7,7-tetramethyl-3-(m-chlorophenyl)-furo[3,4-e]-as-triazine-4-oxide,
j. 5,7-dihydro-5,5,7,7-tetramethyl-3-(p-fluorophenyl)-furo[3,4-e]-as-triazine-4-oxide,
k. 5,7-dihydro-5,5,7,7-tetramethyl-3-(3,5-dinitrophenyl)-furo[3,4-e]-as-triazine-4-oxide, or
l. 5,7-dihydro-5,5,7,7-tetramethyl-3-(3,4-dimethylphenyl)-furo[3,4-e]-as-triazine-4-oxide, respectively.

It will be recognized that the corresponding free bases of Example I are also contemplated within this invention and may be isolated employing conventional techniques.

The 5,7-dihydro-5,5,7,7-tetramethyl-3-phenylfuro[3,4-e]-as-triazine-4-oxide hydrochloride of this example is an effective sleep inducer when orally administered to an animal in need of said treatment at a dosage of 200 mg. just before bedtime.

EXAMPLE 2

5,7-Dihydro-5,5,7,7-tetramethyl-3-phenylfuro[3,4-e]-as-triazine

A mixture of 5.42 g. (0.02 mole) 5,7-dihydro-5,5,7,7-tetramethyl-3-phenylfuro[3,4-e]-as-triazine-4oxide and 70 ml. triethylphosphite is refluxed under nitrogen for 18 hours at a bath temperature of 180° C. The solvent is removed in vacuo and the residue recrystallized from aqueous ethanol to give 5,7-dihydro-5,5,7,7-tetramethyl-3-phenylfuro[3,4-e]-as-triazine, m.p. 90°–91° C.

Following the above procedure and using in place of 5,7-dihydro-5,5,7,7-tetramethyl-3-phenylfuro[3,4-e]-as-triazine-4-oxide an equivalent amount of a. 5,7-dihydro-5,5,7,7-tetramethyl-3-(p-chlorophenyl)-furo[3,4-e]-as-triazine-4-oxide,
b. 5,7,-dihydro-5,5,7,7-tetramethyl-3-(p-tolyl)-furo[3,4-e]-as-triazine-4-oxide,
c. 5,7-dihydro-5,5,7,7-tetramethyl-3-(p-anisyl)-furo[3,4-]-as-triazine-4-oxide,
d. 5,7-dihydro-5,5,7,7-tetramethyl-3-(m-trifluoromethylphenyl)-furo[3,4-e]-as-triazine-4-oxide,
e. 5,7-dihydro-5,5,7,7-tetramethyl-3-(p-aminophenyl)-furo[3,4-e]-as-triazine-4-oxide,
f. 5,7-dihydro-5,5,7,7-tetramethyl-3-(p-nitrophenyl)-furo[3,4-e]-as-triazine-4-oxide,
g. 5,7-dihydro-5,5,7,7-tetramethyl-3-(3,4-dichlorophenyl)-furo[3,4-e]-as-triazine-4-oxide,
h. 5,7-dihydro-5,5,7,7-tetramethyl-3-(m-nitrophenyl)-furo[3,4-e]-as-triazine-4-oxide,
i. 5,7-dihydro-5,5,7,7-tetramethyl-3-(m-chlorophenyl)-furo[3,4-e]-as-triazine-4-oxide,
j. 5,7-dihydro-5,5,7,7-tetramethyl-3-(p-fluorophenyl)-furo[3,4-e]-as-triazine-4-oxide,
k. 5,7-dihydro-5,5,7,7-tetramethyl-3-(3,5-dinitrophenyl)-furo[3,4-e]-as-triazine-4-oxide, or
l. 5,7-dihydro-5,5,7,7-tetramethyl-3-(3,4-dimethylphenyl)-furo[3,4-e]-as-triazine-4-oxide, there is obtained a. 5,7-dihydro-5,5,7,7-tetramethyl-3-(p-chlorophenyl)-furo[3,4-e]-as-triazine, b. 5,7-dihydro-5,5,7,7-tetramethyl-3-(p-tolyl)-furo[3,4-e]-as-triazine,
c. 5,7-dihydro-5,5,7,7-tetramethyl-3-(p-anisyl)-furo[3,4-e]-as-triazine,
d. 5,7-dihydro-5,5,7,7-tetramethyl-3-(m-trifluoromethylphenyl)-furo[3,4-e]-as-triazine,
e. 5,7-dihydro-5,5,7,7-tetramethyl-3-(p-aminophenyl)-furo[3,4-e]-as-triazine,
f. 5,7-dihydro-5,5,7,7-tetramethyl-3-(p-nitrophenyl)-furo[3,4-e]-as-triazine,
g. 5,7-dihydro-5,5,7,7-tetramethyl-3(3,4-dichlorophenyl)-furo[3,4-e]-as-triazine,
h. 5,7-dihydro-5,5,7,7-tetramethyl-3-(m-nitrophenyl)-furo[3,4-e]-as-triazine,
i. 5,7-dihydro-5,5,7,7-tetramethyl-3-(m-chlorophenyl)-furo[3,4-e]-as-triazine,
j. 5,7-dihydro-5,5,7,7-tetramethyl-3-(p-fluorophenyl)-furo[3,4-e]-as-triazine,
k. 5,7-dihydro-5,5,7,7-tetramethyl-3-(3,5-dinitrophenyl)-furo[3,4-e]-as-triazine, or
l. 5,7-dihydro-5,5,7,7-tetramethyl-3(3,4-dimethylphenyl)-furo[3,4-e]-as-triazine, respectively.

The 5,7-dihydro-5,5,7,7-tetramethyl-3-phenylfuro-[3,4-e]-as-triazine of this example is an effective sleep inducer when orally administered to an animal in need of said treatment at a dosage of 200 mg. just before bedtime.

EXAMPLE 3

5,7-Dihydro-5,5,7,7-tetramethyl-3-phenylfuro[3,4-e]-as-triazine

To a solution of 0.271 grams (0.001 mole) 5,7-dihydro-5,5,7,7-tetramethyl-3-phenylfuro-[3,4-e]-as-triazine-4-oxide and 0.246 grams (0.003 mole) cyclohexene in 4 ml. absolute ethanol is added 100 milligrams of 10% palladium on charcoal and the resulting mixture is refluxed under an atmosphere of nitrogen for 18 hours. The catalyst is removed by filtration and the filtrate evaporated to dryness. The residue is recrystallized from ether/hexane to give 5,7-dihydro-5,5,7,7-tetramethyl-3-phenylfuro[3,4-e]-as-triazine, m.p. 90°–91° C.

Following the above procedure and using in place of 5,7-dihydro-5,5,7,7-tetramethyl-3-phenylfuro[3,4-e]-as-triazine-4-oxide an equivalent amount of
a. 5,7-dihydro-5,5,7,7-tetramethyl-3-(p-chlorophenyl)-furo[3,4-e]-as-triazine-4-oxide,
b. 5,7-dihydro-5,5,7,7-tetramethyl-3-(p-tolyl)-furo[3,4-e]-as-triazine-4-oxide,
c. 5,7-dihydro-5,5,7,7-tetramethyl-3-(p-anisyl)-furo[3,4-e]-as-triazine-4-oxide,
d. 5,7-dihydro-5,5,7,7-tetramethyl-3-(m-trifluoromethylphenyl)-furo[3,4-e]-as-triazine-4-oxide,
e. 5,7-dihydro-5,5,7,7-tetramethyl-3-(p-aminophenyl)-furo[3,4-e]-as-triazine-4-oxide,
f. 5,7-dihydro-5,5,7,7-tetramethyl-3-(p-nitrophenyl)-furo[3,4-e]-as-triazine-4-oxide,
g. 5,7-dihydro-5,5,7,7-tetramethyl-3-(3,4-dichlorophenyl)-furo[3,4-e]-as-triazine-4-oxide,
h. 5,7-dihydro-5,5,7,7-tetramethyl-3-m-(nitrophenyl)-furo[3,4-e]-as-triazine-4-oxide,
i. 5,7-dihydro-5,5,7,7-tetramethyl-3-(m-chlorophenyl)-furo[3,4-e]-as-triazine-4-oxide, or
j. 5,7-dihydro-5,5,7,7-tetramethyl-3-(p-fluorophenyl)-furo[3,4-e]-as-triazine-4-oxide,
k. 5,7-dihydro-5,5,7,7-tetramethyl-3-(3,5-dinitrophenyl)-furo[3,4-e]-as-triazine-4-oxide, or
l. 5,7-dihydro-5,5,7,7-tetramethyl-3-(3,4-dimethylphenyl)-furo[3,4-e]-as-triazine-4-oxide, there is obtained a. 5,7-dihydro-5,5,7,7-tetramethyl-3-(p-chlorophenyl)-furo[3,4-e]-as-triazine,
b. 5,7-dihydro-5,5,7,7-tetramethyl-3-(p-tolyl)-furo[3,4-e]-as-triazine,
c. 5,7-dihydro-5,5,7,7-tetramethyl-3-(p-anisyl)-furo[3,4-e]-as-triazine,
d. 5,7-dihydro-5,5,7,7-tetramethyl-3-(m-trifluoromethylphenyl)-furo[3,4-e]-as-triazine,
e. 5,7-dihydro-5,5,7,7-tetramethyl-3-(p-aminophenyl)-furo[3,4-e]-as-triazine,
f. 5,7-dihydro-5,5,7,7-tetramethyl-3-(p-nitrophenyl)-furo[3,4-e]-as-triazine,
g. 5,7-dihydro-5,5,7,7-tetramethyl-3-(3,4-dichlorophenyl)-furo[3,4-e]-as-triazine,
h. 5,7-dihydro-5,5,7,7-tetramethyl-3-(m-nitrophenyl)-furo[3,4-e]-as-triazine,
i. 5,7-dihydro-5,5,7,7-tetramethyl-3-(m-chlorophenyl)-furo[3,4-e]-as-triazine,
j. 5,7-dihydro-5,5,7,7-tetramethyl-3-(p-fluorophenyl)-furo[3,4-e]-as-triazine,
k. 5,7-dihydro-5,5,7,7-tetramethyl-3-(3,5-dinitrophenyl)-furo[3,4-e]-as-triazine, or
l. 5,7-dihydro-5,5,7,7-tetramethyl-3-(3,4-dimethylphenyl)-furo[3,4-e]-as-triazine, respectively.

EXAMPLE 4

5,7-Dihydro-5,5,7,7-tetramethyl-3-(m-nitrophenyl)-furo[3,4-e]-as-triazine-4-oxide A mixture of 6.84 g. (0.04 mole) 2,2,5,5-tetramethyl-3,4(2H,5H)-furandione-3-hydrazone-4-oxime and 16.14 g. (0.06 mole) m-nitrotriethylorthobenzoate is heated under nitrogen for 24 hours at a bath temperature of 140° C. during which time all distillate is removed. The mixture is cooled to 25° C. and 250 ml. of ether is added. The resulting solid is removed by filtration and the filtrate evaporated to dryness in vacuo at 100° C. The resulting residue is recrystallized from methylene chloride/hexane to give 5,7-dihydro-5,5,7,7tetramethyl-3-(m-nitrophenyl)-furo[3,4-e]-as-triazine-4-oxide, m.p. 202°–204° C.

EXAMPLE 5

5,7-Dihydro-5,5,7,7-tetramethyl-3-(m-nitrophenyl)-furo[3,4-e]-as-triazine-4-oxide To a mixture of 0.2 ml (0.005 mole) of fuming nitric acid and 1.5 grams (0.01 mole) of trifluoromethanesulfonic acid in 15 ml. anhydrous methylene chloride, after allowing the resulting mixture to be stirred for 1 hour at 25° C., there is added dropwise maintaining the temperature at −30° C., 0.542 grams (0.002 mole) of 5,7-dihydro-5,5,7,7-tetramethyl-3-phenylfuro[[3,4-e]-as-triazine-4-oxide in 15 ml. of anhydrous methylene chloride. The resulting heterogeneous mixture is stirred at 25° C. for 72 hours, poured onto ice, and neutralized with solid sodium bicarbonate. The organic layer is removed and the aqueous phase extracted several times with methylene chloride. The combined organic layers are washed with saturated aqueous sodium chloride solution, dried over magnesium sulfate and evaporated to give a white solid. The resulting solid is recrystallized from methylene chloride/hexane to give 5,7-dihydro-5,5,7,7-tetramethyl-3-(m-nitrophenyl)-furo[3,4-e]-as-triazine-4-oxide, m.p. 202°–204° C.

Following the above procedure but using in place of 5,7-dihydro-5,5,7,7-tetramethyl-3-phenylfuro[3,4-e]-as-triazine-4-oxide, an equivalent amount of a. 5,7-dihydro-5,5,7,7-tetramethyl-3-(p-tolyl)furo[3,4-e]-as-triazine-4-oxide, or
b. 5,7-dihydro-5,5,7,7-tetramethyl-3-(p-anisyl)-furo[3,4-e]-as-triazine-4-oxide, there is obtained a. 5,7-dihydro-5,5,7,7-tetramethyl-3-(4-methyl-3-nitrophenyl)-furo[3,4-e]-as-triazine-4-oxide, and
b. 5,7-dihydro-5,5,7,7-tetramethyl-3-(4-methoxy-3-nitrophenyl)-furo[3,4-e]-as-triazine-4-oxide, respectively.

The 5,7-dihydro-5,5,7,7-tetramethyl-3-(m-nitrophenyl)-furo[3,4-e]-as-triazine-4-oxide of this example is an effective sleep inducer when orally administered to an animal in need of said treatment at a dosage of 200 mg. just before bedtime.

What is claimed is:

1. A method of inducing sleep in animals which comprises administering to an animal in need of such treatment a sleep-inducing effective amount of a compound of the formula

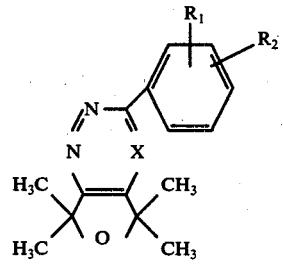

wherein
$R_1$ and $R_2$ each independently represent hydrogen, halo having an atomic weight of about 19 to 36, lower alkyl, straight chain lower alkoxy, amino, nitro or trifluoromethyl, and
X represents

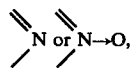

provided that
i. when one of $R_1$ and $R_2$ represents nitro, the other is other than nitro or trifluoromethyl;
ii. when $R_1$ and $R_2$ represent trifluoromethyl, they are on other than adjacent carbon atoms, and
iii. when $R_1$ and $R_2$ represent t-butyl, they are on other than adjacent carbon atoms, and
iv. when one of $R_1$ and $R_2$ is trifluoromethyl and the other is t-butyl, they are on other than adjacent carbon atoms.

2. A method of treating tension in animals which comprises administering to an animal in need of such treatment a tranquilizing effective amount of a compound of the formula

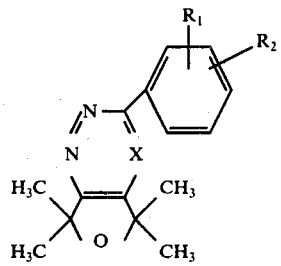

wherein
$R_1$ and $R_2$ each independently represent hydrogen, halo having an atomic weight of about 19 to 36, lower alkyl, straight chain lower alkoxy, amino, nitro or trifluoromethyl, and
X represents

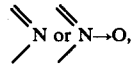

provided that
i. when one of $R_1$ and $R_2$ represents nitro, the other is other than nitro or trifluoromethyl;
ii. when $R_1$ and $R_2$ represent trifluoromethyl, they are on other than adjacent carbon atoms, and
iii. when $R_1$ and $R_2$ represent t-butyl, they are on other than adjacent carbon atoms, and
iv. when one of $R_1$ and $R_2$ is trifluoromethyl and the other is t-butyl, they are on other than adjacent carbon atoms.

3. A pharmaceutical composition for use in treating tension or inducing sleep comprising a therapeutically effective amount of a compound of the formula

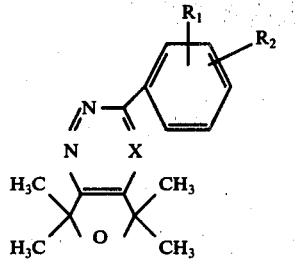

wherein
$R_1$ and $R_2$ each independently represent hydrogen, halo having an atomic weight of about 19 to 36, lower alkyl, straight chain lower alkoxy, amino, nitro or trifluoromethyl, and
X represents

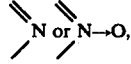

provided that
i. when one of $R_1$ and $R_2$ represents nitro, the other is other than nitro or trifluoromethyl;
ii. when $R_1$ and $R_2$ represent trifluoromethyl, they are on other than adjacent carbon atoms, and
iii. when $R_1$ and $R_2$ represent t-butyl, they are on other than adjacent carbon atoms, and
iv. when one of $R_1$ and $R_2$ is trifluoromethyl and the other is t-butyl, they are on other than adjacent carbon atoms, in association with a pharmaceutically acceptable diluent or carrier therefor.

* * * * *